United States Patent [19]

Farcasiu

[11] Patent Number: 4,629,817
[45] Date of Patent: Dec. 16, 1986

[54] TRANSFER OF CYCLOALKYL GROUPS BY TRANSALKYLATION OF AROMATICS

[75] Inventor: Malvina Farcasiu, Flemington, N.J.

[73] Assignee: Mobil Oil Corporation, New York, N.Y.

[21] Appl. No.: 730,962

[22] Filed: May 6, 1985

[51] Int. Cl.[4] .............................................. C07C 5/22
[52] U.S. Cl. .................................. 585/470; 585/471; 585/474
[58] Field of Search ....................... 585/470, 471, 474

[56] References Cited

U.S. PATENT DOCUMENTS 4,317,712  3/1982  Farcasiu ............................ 208/46
4,484,011  11/1984 Van Sickle ........................ 568/781
4,508,618  4/1985  Olah ................................. 208/134

Primary Examiner—Curtis R. Davis
Attorney, Agent, or Firm—Alexander J. McKillop; Michael G. Gilman; Edward F. Kenehan, Jr.

[57] ABSTRACT

There is provided a process for transferring cycloalkyl groups from donor to acceptor aromatic molecules. The process involves the use of a Brönstëd acid catalyst such as trifluoromethanesulfonic acid.

3 Claims, 1 Drawing Figure

TRANSFER OF CYCLOALKYL GROUPS BY TRANSALKYLATION OF AROMATICS

BACKGROUND

This invention relates to the transfer of cycloalkyl groups by transalkylation of aromatics.

Transalkylation reactions are a useful means for transferring alkyl groups from one aromatic compound to another. In the Farcasiu U.S. Pat. No. 4,317,712, heavy petroleum oils, such as vacuum resids, and heavy fractions of tar sands and shale oil, are partially converted to more volatile hydrocarbons by mixing with light aromatic hydrocarbons and treatment of the mixture with a Friedel-Crafts catalyst such as aluminum chloride. It it believed that the conversion found is essentially a transalkylation, i.e. the resid undergoes dealkylation with concurrent alkylation of the light aromatic hydrocarbon. In addition to aluminum trichloride, trifluoromethanesulfonic acid is also suggested as being a suitable catalyst for the process described in U.S. Pat. No. 4,317,712. Note column 5, lines 16–19 and Example 8.

A number of known and useful compounds contain cycloalkyl groups bound to an aromatic ring. Examples of such compounds include phenylcyclohexane, phenylcyclopentane and dinitrocyclohexylphenol. Accordingly, methods for preparing such compounds are needed.

SUMMARY

According to one aspect of the invention, there is provided a process for transferring alkyl groups from donor compounds to acceptor compounds by a transalkylation reaction, said donor compounds being aromatic compounds having said alkyl groups substituted on aromatic rings thereof, said acceptor compounds being aromatic compounds not having said alkyl groups substituted on aromatic rings thereof, said process comprising contacting sufficient amounts of said donor and acceptor compounds and a catalytically effective amount of a Bronsted acid catalyst such as trifluoromethanesulfonic acid under sufficient transalkylating conditions, whereby essentially all of said alkyl groups which are transferred are cycloalkyl groups, said transfer taking place essentially without isomerization of the saturated ring of the cycloalkyl group. The molar ratio of donor:acceptor:acid may be, e.g., about 1:2–10:0.2–0.5.

EXAMPLE

Figure 1:
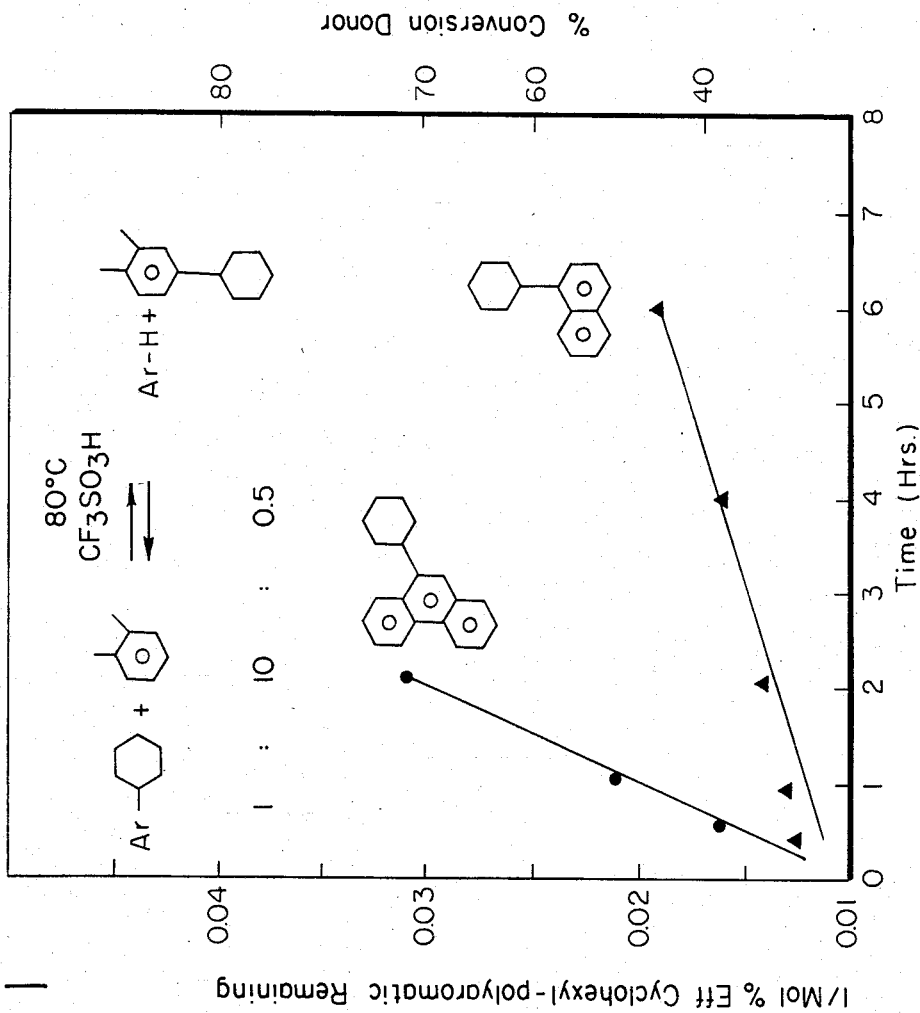
FIG. 1 is a graph depicting results of various transalkylation reactions in accordance with the present invention.

Cycloalkylarenes, more particularly 1-cyclohexylnapthalene and 9-cyclohexylphenanthrene, respectively, were mixed with ortho-xylene and trifluoromethanesulfonic acid in a ratio of 1:10:0.5. More particularly, these reactants were mixed at 25° C. in a round-bottomed flask, equipped with an immersed thermometer, a reflux condenser topped with a drying tube (Drierite) and a magnetic stirring bar. The reactions were conducted at 80° C. by heating the flask quickly to that temperature, and after that (5–10 min) the first sample was withdrawn. The composition at that moment was taken as the starting point for a kinetic study. In fact, very little conversion occurred during heating.

The aliquat samples were quenched in aqueous sodium hydroxide and the hydrocarbon phase was isolated and dried (CaSO$_4$) before analysis.

Product analysis was accomplished by GLC on a 6'×⅛ in OD stainless steel column, with 3% OV17 on 80/100 Supelcoport, and by GLC-MS on a Hewlett-Packard 5992A instrument, equipped with a 50 m OV-101 SCOT column.

Results are summarized in FIG. 1.

Without wishing to be bound by any particular theory, it is noted that the transfer of cyclohexyl groups occurs without isomerization of the saturated ring. Together with the equality of kinetic order in donor, this finding theoretically indicates that the same mechanism operates for the transfer of n-alkyl and cycloalkyl groups. On the other hand, partial isomerization has been observed in the reaction of sec-alkylbenzenes with benzene. Note Burwell, R. L., Jr., Shields, A. D., *J. Am. Chem. Soc.*, 1955, 77, 2766.

What is claimed is:

1. A process for transferring alkyl groups from donor compounds to acceptor compounds by a transalkylation reaction, said donor compounds being aromatic compounds having said alkyl groups substituted on aromatic rings thereof, said acceptor compounds being aromatic compounds not having said alkyl groups substituted on aromatic rings thereof, said process comprising contacting sufficient amounts of said donor and acceptor compounds and a catalytically effective amount of a Bronsted acid catalyst at a sufficient transalkylating temperature, whereby essentially all of said alkyl groups which are transferred are cycloalkyl groups, said transfer taking place essentially without isomerization of the saturated ring of the cycloalkyl group.

2. A process according to claim 1, wherein said Bronsted acid catalyst is trifluoromethanesulfonic acid.

3. A process according to claim 2, wherein the molar ratio of donor:acceptor:acid is about 1:2–10:0.2–0.5.

* * * * *